United States Patent
Weaver et al.

(10) Patent No.: US 9,616,091 B2
(45) Date of Patent: Apr. 11, 2017

(54) METHODS AND COMPOSITIONS CONTAINING AT LEAST 30% IGG AND 10% OR LESS BY WEIGHT IGA FOR REDUCING LUNG INFLAMMATION IN AN ANIMAL

(75) Inventors: Eric Weaver, Ankeny, IA (US); Joy Campbell, Ankeny, IA (US); Louis Russell, Ankeny, IA (US); Miquel Moreto Pedragosa, Barcelona (ES); Anna Perez-Bosque, Barcelona (ES); Francisco Javier Polo Pozo, Barcelona (ES); Joseph Crenshaw, Ankeny, IA (US)

(73) Assignee: THE LAURIDSEN GROUP, INC., Ankeny, IA (US)

( * ) Notice: Subject to any disclaimer, the term of this patent is extended or adjusted under 35 U.S.C. 154(b) by 1179 days.

(21) Appl. No.: 12/992,913

(22) PCT Filed: May 22, 2009

(86) PCT No.: PCT/US2009/045027
§ 371 (c)(1),
(2), (4) Date: Dec. 9, 2010

(87) PCT Pub. No.: WO2009/143453
PCT Pub. Date: Nov. 26, 2009

(65) Prior Publication Data
US 2011/0135581 A1  Jun. 9, 2011

Related U.S. Application Data

(60) Provisional application No. 61/055,870, filed on May 23, 2008.

(51) Int. Cl.
*A61K 35/16* (2015.01)

(52) U.S. Cl.
CPC .................................. *A61K 35/16* (2013.01)

(58) Field of Classification Search
None
See application file for complete search history.

(56) References Cited

U.S. PATENT DOCUMENTS

| | | | |
|---|---|---|---|
| 6,004,576 A | 12/1999 | Weaver et al. | |
| 2003/0099633 A1 | 5/2003 | Campbell et al. | |
| 2003/0103962 A1 | 6/2003 | Campbell et al. | |
| 2003/0190314 A1 | 10/2003 | Campbell et al. | |
| 2004/0063912 A1* | 4/2004 | Blumberg et al. | 530/351 |
| 2004/0146565 A1 | 7/2004 | Strohbehn et al. | |
| 2004/0202660 A1 | 10/2004 | Campbell et al. | |
| 2005/0271674 A1* | 12/2005 | Campbell et al. | 424/184.1 |
| 2008/0138340 A1 | 6/2008 | Campbell et al. | |
| 2008/0213263 A1 | 9/2008 | Campbell et al. | |
| 2009/0110679 A1* | 4/2009 | Li et al. | 424/133.1 |
| 2010/0215667 A1 | 8/2010 | Campbell et al. | |

FOREIGN PATENT DOCUMENTS

| | | |
|---|---|---|
| EP | 0 506 651 A2 | 9/1992 |
| JP | 56 053622 A | 5/1981 |
| WO | WO 2008077022 A2 * | 6/2008 |

OTHER PUBLICATIONS

Campbell et al., Efficacy of Spray-Dried Bovine Serum on Health and Performance of Turkeys Challenged with Pasteurella multocida, J. Appl. Poult. Res., 2004, 13:388-393, Poultry Science Association, Inc.

* cited by examiner

*Primary Examiner* — Michael Szperka
(74) *Attorney, Agent, or Firm* — Buchanan Ingersoll & Rooney PC

(57) ABSTRACT

The present invention provides methods for reducing, attenuating, diminishing, preventing or inhibiting pulmonary inflammation in an animal by orally administering a plasma fraction comprising at least 30% by weight IgG and 10% or less by weight IgA to said animal prior to or following exposure or challenge of the animal to an endotoxin.

6 Claims, 15 Drawing Sheets

METHODS AND COMPOSITIONS CONTAINING AT LEAST 30% IGG AND 10% OR LESS BY WEIGHT IGA FOR REDUCING LUNG INFLAMMATION IN AN ANIMAL

BACKGROUND OF THE INVENTION

The primary source of nutrients for the body is blood, which is composed of highly functional proteins including immunoglobulin, albumin, fibrinogen and hemoglobin. Immunoglobulins are products of mature B cells (plasma cells) and there are five distinct immunoglobulins referred to as classes: M, D, E, A, and G. IgG is the main immunoglobulin class in blood. Intravenous administration of immunoglobulin products has long been used to attempt to regulate or enhance the immune system. Most evidence regarding the effects of intravenous IgG on the immune system suggests the constant fraction (Fc) portion of the molecule plays a regulatory function. The specific antigen binding properties of an individual IgG molecule are conferred by a three dimensional steric arrangement inherent in the amino acid sequences of the variable regions of two light and two heavy chains of the molecule. The constant region can be separated from the variable region if the intact molecule is cleaved by a proteolytic enzyme such as papain. Such treatment yields two fractions with antibody specificity (Fab fractions) and one relatively constant fraction (Fc).

sIgA is the predominant immunoglobulin class secreted onto mucosal surfaces through body fluids such as saliva, tears, milk, bronchoalveolar fluid, and other secretions. IgA has previously been shown to possess anti-inflammatory characteristics. See e.g. Wolf H M, et al. (1994), Human serum IgA downregulates the release of inflammatory cytokines (tumor necrosis factor-alpha, Interleukin-6) in human monocytes, Blood 83:1278-1288. In contrast, the same authors did not demonstrate the anti-inflammatory effects for an IgG-containing composition. IgA does not exist in concentrations in blood or milk to facilitate sufficient concentration for oral administration. In addition, immunoglobulin of any class is to large of a molecule to permit absorption to achieve therapeutic effects after oral administration. Oral immunoglobulin has been shown to be beneficial for treatment of gastrointestinal disease and other gastrointestinal conditions but neither anti-infective nor anti-inflammatory effects have been demonstrated in pulmonary tissue. Thus, the fact that IgA is anti-inflammatory does not allow it to be used as a suitable treatment of pulmonary inflammation.

Numerous cells in the body have distinct membrane receptors for the Fc portion of an IgG molecule (Fcr). Although some Fcr receptors bind free IgG, most bind it more efficiently if an antigen is bound to the antibody molecule. Binding an antigen results in a configurational change in the Fc region that facilitates binding to the receptor. A complex interplay of signals provides balance and appropriateness to an immune response generated at any given time in response to an antigen. Antigen specific responses are initiated when specialized antigen presenting cells introduce antigen, forming a complex with the major histocompatibility complex molecules to the receptors of a specific helper inducer T-cells capable of recognizing that complex. IgG appears to be involved in the regulation of both allergic and autoimmune reactions. Intravenous immunoglobulin for immune manipulation has long been proposed but has achieved mixed results in treatment of disease states. A detailed review of the use of intravenous immunoglobulin as drug therapy for manipulating the immune system is described in Vol. 326, No. 2, pages 107-116, New England Journal of Medicine Dwyer, John M., the disclosure of which is hereby incorporated by reference.

Lipopolysaccharide (LPS), also commonly referred to as endotoxin, a major proinflammatory glycolipid component of the gram-negative bacterial cell wall, is one of the agents ubiquitously present as contaminant on airborne particles, including air pollution, organic dusts, and cigarette smoke. Chronic exposure to significant levels of LPS is reported to be associated with the development and/or progression of many types of lung diseases, including asthma, chronic bronchitis, and progressive irreversible airflow obstruction, that are all characterized by chronic inflammatory processes in the lung.

There is a continuing effort and need in the art for improved compositions and methods for reducing the effects of LPS and other inflammatory components in the lungs that do not require higher levels of IgA. It is therefore an object of the present invention to provide methods and pharmaceutical compositions for treating animals with pulmonary immune dysfunction disease states.

It is yet another object of the invention to provide a novel pharmaceutical composition comprising purified plasma that includes concentrated levels of immununoglobulins.

It is still a further object of the invention to provide a novel pharmaceutical composition comprising purified plasma that is substantially free of IgA.

These and other objects of the invention will become apparent from the detailed description of the invention which follows.

SUMMARY OF THE INVENTION

According to the invention, applicants have identified purified and isolated-plasma, components, and derivatives thereof, which are useful as a pharmaceutical composition for reducing pulmonary inflammation in animals, including humans. According to the invention, a plasma composition comprising immunoglobulin including concentrated levels of IgG, when administered orally, reduces pulmonary inflammation, and induces a lowering of pro-inflammatory cytokines such as TNF-α levels relative to animals not orally fed immunoglobulin or plasma fractions.

The invention includes the administration of a plasma fraction (PF) that includes concentrated levels of immunoglobulins, such as IgA, IgM, and especially IgG. In one embodiment of the invention, the PF contains undetectable levels of IgA. The composition of the invention is surprisingly effective in preventing and/or reducing pulmonary inflammation, including LPS-induced monocyte activation in bronco-alveolar lavage fluid and LPS-induced leukocyte stimulation in lung tissue, even following oral administration. This is unexpected as traditionally it was thought that plasma proteins such as immunoglobulins, must be introduced intravenously to suppress inflammatory disease.

DETAILED DESCRIPTION OF THE INVENTION

Figure 1:
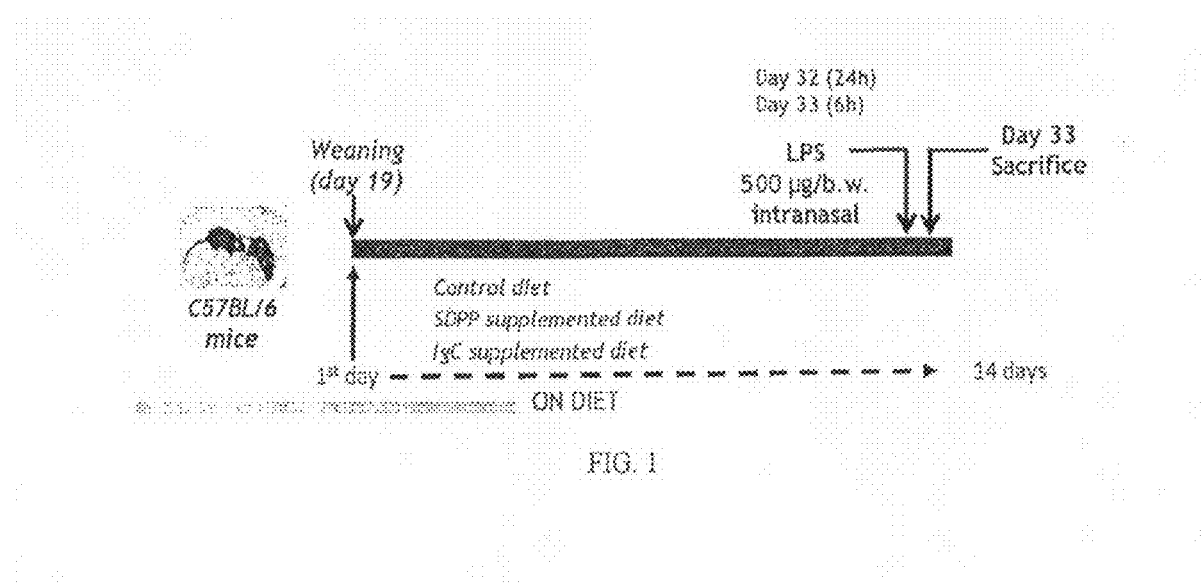
FIG. 1 illustrates the experimental protocol for Example 1.

According to the invention, Applicant has provided herein a pharmaceutical composition comprising immunoglobulin components purified and concentrated from animal plasma which are useful in reducing pulmonary inflammation in animals, including LPS-induced pulmonary inflammation.

According to the invention, gamma-globulin isolated from animal sources such as serum, plasma, egg, or milk is administered orally for treatment of LPS-induced lung inflammation. Quite surprisingly, oral administration of this composition has been found to substantially decrease LPS-induced monocyte activation in bronchoalveolar lavage fluid (BALF) and further prevent LPS-induced leukocyte stimulation in lung tissue.

As used herein with reference to the composition of the invention, the terms "plasma", "globulin", "gamma-globulin", and "immunoglobulin" will all be used. These are all intended to describe a composition purified from animal sources including blood, egg, or milk-which retains the Fc region of the immunoglobulin molecule. This also includes transgenic recombinant immunoglobulins purified from transgenic bacteria, plants or animals. This can be administered by spray-dried plasma, or globulin which has been further purified therefrom, or any other source of serum globulin which is available. Further, as used herein, the terms "PF" (or "Plasma Fraction") and "IgC" ("Immunoglobulin Concentrate") are interchangeable, and refer to a plasma fraction where the fibrin and albumin have been removed from the plasma. Thus, both PF and IgC refer to a plasma fraction where the fibrin and albumin have been removed from the plasma. One such source of purified globulin is ImmunoLin® available from Proliant Inc.

Globulin may be purified according to any of a number of methods available in the art, including those described in Akita, B. M. and S, Nakai. 1993. Comparison of four purification methods for the production of immunoglobulins from eggs laid by hens immunized with an enterotoxigenic E. coli strain. Journal of Immunological Methods 160:207-214; Steinbuch, M. and R. Audran. 1969. The isolation of IgG from mammalian sera with the aid of caprylic acid. Archives of Biochemistry and Biophysics 134:279-284; Lee, Y., T. Aishima, S, Nakai, and J. S. Sim. 1987. Optimization for selective fractionation of bovine blood plasma proteins using polyethylene glycol). Journal of Agricultural and Food Chemistry 35:958-962; Poison, A., G. M. Potgieter, J. F. Langier, G. E. F. Mears, and F. J. Toubert. 1964. Biochem. Biophys. Acta. 82:463-475.

Animal plasma from which immunoglobulin or other plasma fractions may be isolated include pig, bovine, ovine, poultry, equine, or goat plasma. Additionally, applicants have identified that cross species sources of the gamma globulins still provides the effects of the invention.

Concentrates of the product can be obtained by spray drying, lyophilization, or any other drying method that does not cause the plasma to lose its ability to reduce LPS-induced pulmonary inflammation. As used herein, the term "SDAP" refers to spray-dried animal plasma from any source. As used herein, spray-dried plasma protein (SDPP) is a complex mixture of active proteins and other biologically important compounds derived from plasma of any species that are spray-dried. In accordance with certain embodiments of the invention, SDAP and SDPP may be used interchangeably, or may be used separately or individually. The concentrates may also be used in their liquid or frozen form.

The active ingredient may also be microencapsulated, protecting and stabilizing from high temperature, oxidants, pH-like humidity, etc. The pharmaceutical compositions of the invention can be in tablets, capsules, ampules for oral use, granulate powder, cream, both as a unique ingredient and associated with other excipients or active compounds, or even as a feed additive.

One method of achieving a gamma-globulin composition concentrate of the invention is as follows although the globulin may be delivered as a component of plasma.

The immunoglobulin concentrate is derived from animal blood. The source of the blood can be from any animal that has blood which includes plasma and immunoglobulins. For convenience, blood from beef, pork, and poultry processing plants is preferred. Anticoagulant is added to whole blood and then the blood is centrifuged to separate the plasma. Any anticoagulant may be used for this purpose, including sodium citrate and heparin. Persons skilled in the art can readily appreciate such anticoagulants. Calcium or other suitable reagent to react with fibrinogen is then added to the plasma to promote clotting, the conversion of fibrinogen to fibrin, or to facilitate the removal of fibrinogen; however other methods are acceptable. This mixture is then centrifuged to remove the fibrin portion.

Once the fibrin is removed from plasma resulting in serum, the serum can be used as a principal source of Ig. Alternatively, one could also inactivate this portion of the clotting mechanism using various anticoagulants.

The defibrinated plasma is next treated with an amount of salt compound or polymer sufficient to precipitate the albumin or globulin fraction of the plasma. Examples of phosphate compounds which may be used for this purpose include all polyphosphates, including sodium hexametaphosphate and potassium polyphosphate. The globulin may also be isolated through the addition of polyethylene glycol or ammonium sulfate.

Following the addition of the phosphate compound, the pH of the plasma solution is lowered to stabilize the albumin precipitate. The pH should not be lowered below 3.5, as this will cause the proteins in the plasma to become damaged. Any type of acid can be used for this purpose, so long as it is compatible with the plasma solution. Persons skilled in the art can readily ascertain such acids. Examples of suitable acids include, but are not limited to, HCl, acetic acid, $H_2SO_4$, citric acid, and $H_2PO_4$. The acid is added in an amount sufficient to lower the pH of the plasma to the designated range. Generally, this amount will range from a ratio of about 1:4 to 1:2 acid to plasma. The plasma is then centrifuged to separate the globulin fraction from the albumin fraction.

The next step in the process is to raise the pH of the globulin fraction with a base until it is no longer corrosive to separation equipment. Acceptable bases for this purpose include NaOH, KOH, and other alkaline bases. Such bases are readily ascertainable by those skilled in the art. The pH of the globulin fraction is raised until it is within a non-corrosive range which will generally be between 5.0 and 9.0. A preferred method of manufacturing the plasma fraction of the application is set forth in U.S. patent application Ser. No. 10/470,982, the disclosure of which is incorporated herein by reference.

The final immunoglobulin concentrate can optionally be spray-dried or lyophilized into a powder. The powder allows for easier packaging and the product remains stable for a longer period of time than the raw globulin concentrate in liquid or frozen form. The preferred immunoglobulin concentrate powder has been found to contain approximately 40-55% by weight IgG, 1-2% by weight IgA, and 6-8% by weight IgM. At a minimum, the immunoglobulin concentrate of the invention should contain at least 50% by weight IgG, with at least 50% by weight IgG being preferred, and at least 55% by weight being most preferred. At a minimum, the concentrate should contain at least about 30% by weight IgG and no more than about 10% by weight IgA. In one embodiment of the invention, the immunoglobulin concentrate does not contain detectable levels of IgA.

In addition to administration with conventional carriers, active ingredients may be administered by a variety of specialized delivery drug techniques which are known to those of skill in the art.

Those skilled in the medical arts will readily appreciate that the doses and schedules of the immunoglobulin will vary depending on the age, health, sex, size and weight of the patient rather than administration, etc. These parameters can be determined for each system by well-established procedures and analysis e.g., in phase I, II, and III clinical trials.

In accordance with certain embodiments of the invention, the immunoglobulin concentrate may be administered through oral consumption in an amount sufficient to reduce, attenuate, or inhibit LPS-induced pulmonary inflammation. In this regard, Ig concentrate (IgC) should be administered to provide 10 mg IgC per kg BW to 250 mg IgC per kg BW. Otherwise, the Ig concentrate (IgC) may be administered to provide a dose up at least 10 mg per kg body weight per day, with at least 30 mg per kg per day being preferred and at least 50 mg per kg per day being more preferred. The IgC may be administered to provide a maximum dose of up to 50 g per day, with 500 mg per kg per day being preferred and 300 mg per kg body weight per day being more preferred. As used herein, the term "LPS-induced pulmonary inflammation" means that inflammation resulting from LPS which causes an elevation in the levels of one or more inflammatory factors in portions of the lungs, including lung tissue and broncoalveolar lavage fluid (BALF). Such inflammatory factors include increased levels of monocytes, leukocytes, TGFβ1, IL-1a, IL-1b, IL-2, IL-4, IL-6, IL-12 (p40), and TNF-α.

For other modes of pharmaceutical administration, such as oral, intravenous, intramuscular, intrapulmonary (e.g. aerosolized for inhalation), intrathecal, sublingual, intrabuccal, subcutaneous, etc. the immunoglobulin concentrate may be dosed at a level sufficient to reduce LPS-induced pulmonary inflammation. A typical dosing range for an adult would be from about 500 mg to 20 g of IgC per day. The daily oral doses are preferably divided and administered twelve hours apart, or twice a day, in a dose preferably ranging from about 5 g to 20 g per day. More frequent dosing regimes may be necessary for optimum effectiveness.

The plasma fraction of the invention may also be used in the prevention of pulmonary inflammation. In this regard, the plasma fraction may be administered prior to exposure to a chemical irritant, environmental factor, or other circumstance that is expected to trigger pulmonary inflammation. For such preventative treatment, the plasma fraction may be administered up to several weeks in advance of the inflammatory trigger at the same doses described above or lower to provide at least some protection against the expected inflammatory response.

Aerosolized compositions for administration are well known in the art, and generally should be sterile, isotonic, preservative free, and pH balanced to 6.0, similar to the airway epithelium to avoid bronchial irritation. The aerosolized compositions may be administered by means of a nebulizing device. Different such devices are available for inhalation therapy, including metered-dose inhalers (MDI), dry-powder inhalers, jet nebulizers, and ultrasonic nebulizers.

The globulin concentrate can be combined with a pharmaceutically acceptable carrier such as a suitable liquid vehicle or excipient and an optional auxiliary additive or additives. The liquid vehicles and excipients are conventional and are commercially available. Illustrative thereof are distilled water, physiological saline, aqueous solutions of dextrose and the like.

The plasma fraction of this invention may be administered alone or in conjunction with other therapeutic agents used in the treatment of pulmonary diseases and conditions, either in a kit for combination therapy or combined in the same pharmaceutical dosage form. Such additional therapeutic agents would include, but are not limited to, antihistamines, decongestants, antiinflammatories, antibiotics, analgesics, antineoplastics, antivirals, bronchodilators, corticosteroids, NSAIDs, etc. Any type of medication may be used in this regard so long as it is compatible with the plasma fraction and does not substantially limit or decrease its efficacy in the reduction of lung inflammation.

In general, in addition to the active compounds, the pharmaceutical compositions of this invention may contain suitable excipients and auxiliaries which facilitate processing of the active compounds into preparations which can be used pharmaceutically. Oral dosage forms encompass tablets, dragees, and capsules.

The pharmaceutical preparations of the present invention are manufactured in a manner which is itself well known in the art. For example the pharmaceutical preparations may be made by means of conventional mixing, granulating, dragee-making, dissolving, lyophilizing processes. The processes to be used will depend ultimately on the physical properties of the active ingredient used.

Suitable excipients are, in particular, fillers such as sugars for example, lactose or sucrose, mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Dragee cores may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet of dragee coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids; such as fatty oils, liquid paraffin, or liquid polyethylene glycols. In addition stabilizers may be added.

Oral doses of globulin concentrate according to the invention were found to decrease LPS-induced inflammation in pulmonary tissue. The phrase "inflammatory immune response," as used herein, refers to the inflammation-causing response of the immune system to a disease, pathogen, antigen or stress. The phrase "inflammatory immune response" also can mean an inflammatory reaction or an immune reaction. The inflammatory response may occur in mammals, including humans, and may occur in response to a respiratory disease.

Clinical uses of the globulin concentrate include prevention or treatment of a respiratory condition or disease involving LPS-induced inflammation. Such conditions include, but are not limited to, asthma or other constriction of hypersensitive airways; chronic obstructive pulmonary disease (COPD) or other lung disease causing shortness of breath; chronic bronchitis or other inflammation and permanent scarring of the bronchial tubes; emphysema or other damage to air sacs walls causing loss of elasticity; pleurisy or other inflammation of the pleural membrane lining lungs and the chest cavity; lung cancer or malignant tumors that develop in lung tissue; acute bronchitis or other inflammation of the bronchial tubes; acute or chronic inflammation of the alveolar sacs; influenza or other infection caused by the influenza virus; pneumonia caused by virus or bacteria; sinusitis or other inflammation of the sinus cavities; common cold caused by virus or bacteria; cystic fibrosis; respiratory diseases caused by toxins or pollutants or environmental causes; respiratory diseases caused by SARS (severe acute respiratory syndrome), or RSV (respiratory syncytial virus) or other viral agents; tuberculosis or other respiratory disease caused by mycobacteria or other bacteria; or other respiratory disease, including those caused by complications arising from HIV infection or auto-immune disease.

In certain embodiments of the invention, the inflammatory response occurs in the animal and can be observed in the lung tissue or BALF or blood or other component of the animal's body.

As used herein, the word "attenuate" is defined to include, but not be limited to, inhibit, weaken, decrease, impair, reduce, and diminish.

As used herein, the term "antigen" refers to a substance that is capable of illiciting or inducing or stimulating an immune response, and/or reacts specifically with antibodies and/or T cells. An antigen can be of viral or bacterial origin, or can be a substance which is foreign material to a biological system. An antigen may be referred to as an immunogen. LPS, as provided hereinbelow, is one example of an antigen. In certain embodiments of the invention, an endotoxin is an antigen. In other certain embodiment of the invention, an antigen is a component of the causative agent of a respiratory disease. For example, an antigen may be an outer membrane protein or component of a bacterial cell, wherein the bacteria is a causative agent of a disease. An antigen may also be a component of a viral coat, wherein the actual virus is the causative agent of a disease.

As used herein, the term "LPS" is an abbreviation for lipopolysaccharide, which is a macromolecule or compound containing lipid and polysaccharide moieties. LPS may also refer to a group of substances present or commonly found as a major constituent of the cell walls of certain bacteria, including the gram-negative strains. LPS can be highly immunogenic or antigenic in biological systems. As used herein, LPS also refers to lipopolysaccharide macromolecules or molecules, or fragments thereof, or selected portions of thereof.

Oral administration of IgG or other plasma components has tremendous advantages over parenteral administration. The most obvious are the risks associated with intravenous administration including: allergic reactions, the increased risk of disease transfer from human blood such as HIV or hepatitis, the requirement for the same species source, the cost of administration, and the benefits of oral IgG is greater neutralization of endotoxin and the "basal" stimulation of the immune system; the potential use of xenogeneic IgG. The invention provides a non-invasive method of modulating the immune response induced by LPS and other inflammatory factors. This can be used to treat a variety of lung-related conditions and diseases where immunomodulation, immunosuppression or immunoregulation is the desired outcome (organ transfers, chronic immunostimulatory disorders, etc.).

The plasma fraction of the invention has been found to be effective in attenuating and/or inhibiting pulmonary inflammation in various pulmonary components, including in at least the bronco-alveolar lavage fluid (BALF) and the lung tissue. In this regard, the PF has been found to be effective in reducing pulmonary inflammation by multiple modes of action, including reduction of monocyte and leukocyte activation.

The following example is intended to illustrate certain embodiments of the invention without limitation.

Example 1

Lung Inflammation Study

Effects of Spray-Dried Plasma Protein on Nasal Associated Lymphoid Tissue in a Lung Inflammation Model in Mice Since the common mucosal immune system connects the inductive sites (Peyer's patches and Nasal Associated Lymphoid Tissue; NALT) with the effector sites (lamina propria of the intestinal and respiratory tracts), we evaluated the effect of dietary plasma proteins on pulmonary inflammation. This study was conducted to evaluate the extent to which SDPP and PF supplementation may attenuate or inhibit LPS-induced lung inflammation.

Protocol:

C57BL/6 Hsd mice were fed diets supplemented with 8% SDPP (SDPP group), 1.5% PF (immunoglobulin concentrate; PF group) or with milk proteins (Control group) from day 19 (weaning) until day 33. On day 32, mice were given an intranasal dose of 500 LPS/kg b.w. (groups LPS, LPS-SDPP and LPS-PF), or PBS (groups Control, SDPP and PF), and killed 24 h after. (See FIG. 1 for diagram of experimental protocol.)

Experimental Groups:
Group 1: control: administered with PBS+control diet
Group 2: SDPP: administered with PBS+SDPP diet
Group 3: PF: administered with PBS+PF diet
Group 4: LPS: administered with LPS (EC)+control diet
Group 5: LPS-SDPP: administered with LPS (EC)+SDPP diet
Group 6: LPS-PF: administered with LPS (EC)+PF diet Samples:
1. Bronco-alveolar lavage fluid (BALF)
   a) Protein in BALF
   b) Cells in BALF
   c) Phenotypic characterization
   d) cytokine and chemokine release
2. Blood
   a) Number of cells
   b) Phenotypic characterization
3. Lung tissue
   a) Cell infiltration in lung
   b) Phenotypic characterization
   c) Anti-inflammatory and pro-inflammatory mediators Results and Discussion:

The percentage of different subpopulations of lymphocytes and polymorphonuclear cells in broncoalveolar lavage fluid (BALF), in lung tissue, and in blood were determined.

In BALF, LPS administration increased 27-fold the number of leukocytic cells. LPS also modified the profile of the cells in BALF (In Control group, 3% were lymphocytes and 97% polymorphonuclears; in LPS group they were 40% and 60%, respectively; $P<0.001$). Diets supplemented with either SDPP or PF did not modify the LPS response but SDPP prevented in part the LPS-induced activation of monocytes ($P<0.05$). In BALF, LPS increased protein concentration 1.5 fold at 6 hours, and 2.4-4 fold at 24 hours. Additionally in BALF, LPS induced the recruitment of leukocytes, mainly lympocytes. LPS also changed the outline of polymorphonuclear cells toward neutrophil subset. LPS further increased the activation of both monocytes and neutrophils.

Figure 2:
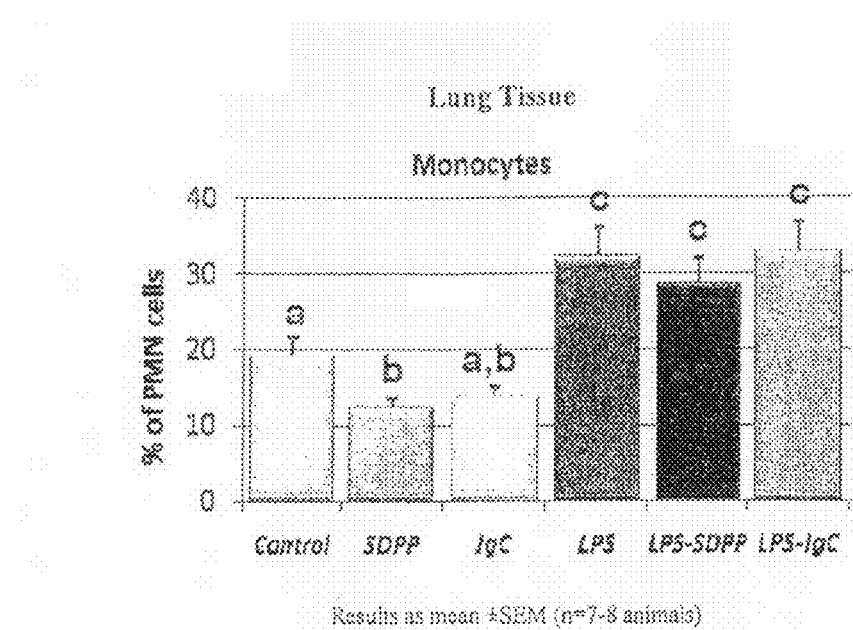
FIG. 2 is a graph depicting modification of LPS-induced activation of monocytes by control, SDPP, PF, LPS, LPS-SDPP, and LPS-PF, in accordance with Example 1.
Figure 3:
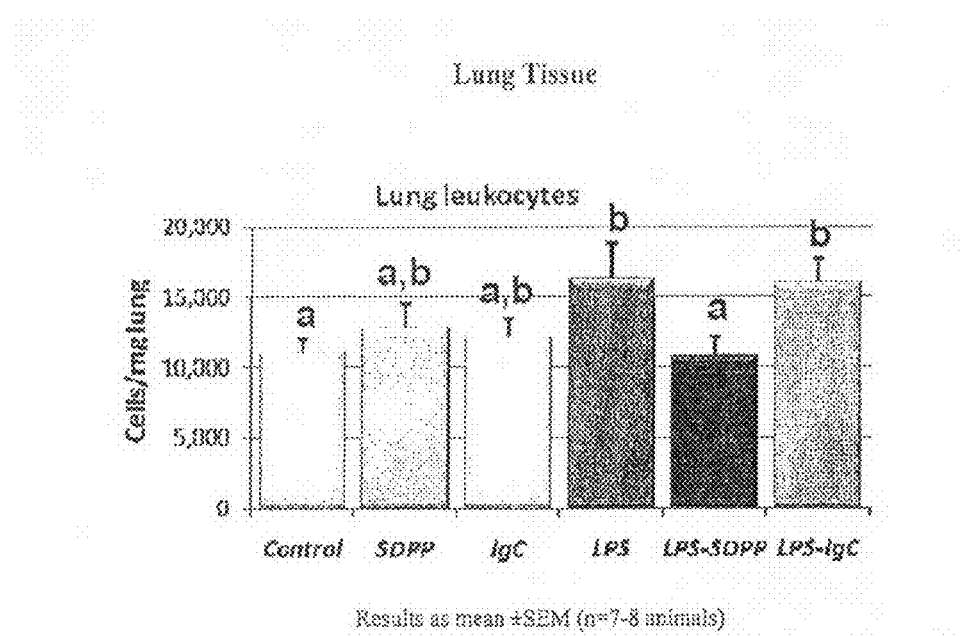
FIG. 3 is a graph depicting modification of LPS-induced activation of lung leukocytes in accordance with Example 1.
Figure 4:
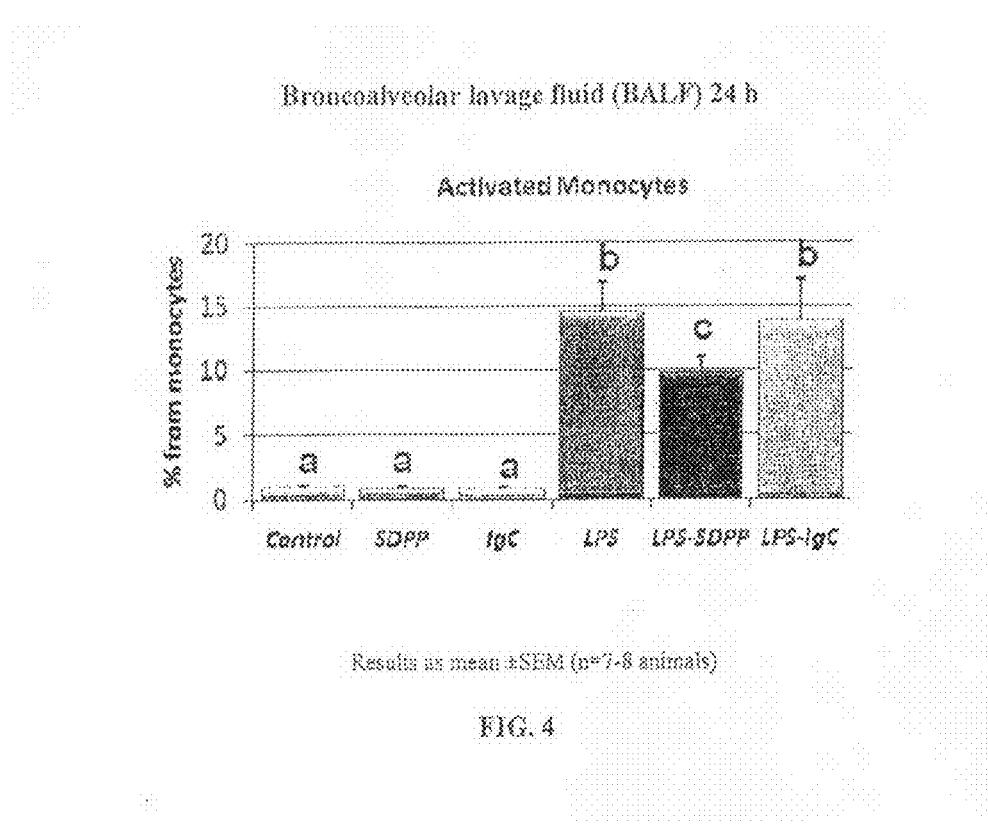
FIG. 4 is a graph depicting modification of LPS-induced activation of monocytes in broncoalveolar lavage fluid (BALF) in accordance with Example 1.
Figure 5:
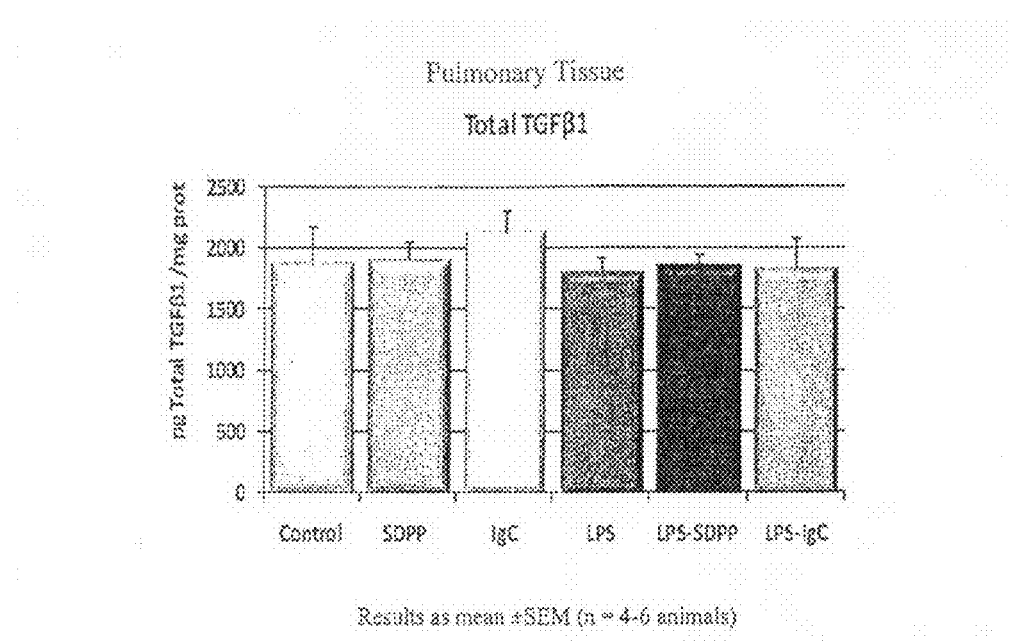
FIG. 5 is a graph depicting modification of total TGFβ1 in accordance with Example 1.
Figure 6:
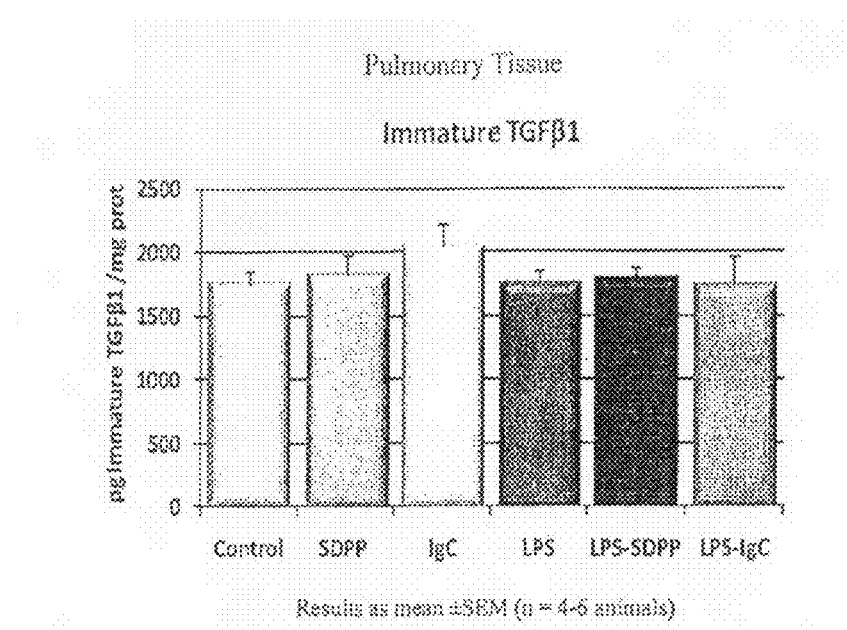
FIG. 6 is a graph depicting modification of immature TGFβ1 in accordance with Example 1.

In lung tissue, LPS increased the percentage of neutrophils and monocytes, resulting in 50% increase of infiltrated granulocytes ($P<0.05$). Supplemented diets did not modify the LPS effects. However, both SDPP and PF diets reduced the percentage of resident neutrophils and monocytes ($P<0.05$) as well as the degree of activation of lung neutrophils ($P<0.05$). (See Plasma protein supplementation reduced innate immune cells from NALT without affecting the pulmonary immune response to LPS. The degree of activation of infiltrated monocytes was in part reduced by SDPP. (FIG. 2). In lung tissue, LPS induced leukocyte recruitment into lung tissue, increasing the number and activation of both polymorphonuclear populations (e.g., monocytes and neutrophils). Also in lung tissue, plasma protein supplementation prevented LPS-induced leukocyte stimulation. (FIG. 3). In control conditions, SDPP reduced the percentage of resident monocytes. (FIG. 4).

In blood, LPS had little effect on blood leukocyte populations. Additionally, in the blood samples, it was found that neither supplement affected LPS-induced effects on blood leukocytes.

Figure 7:
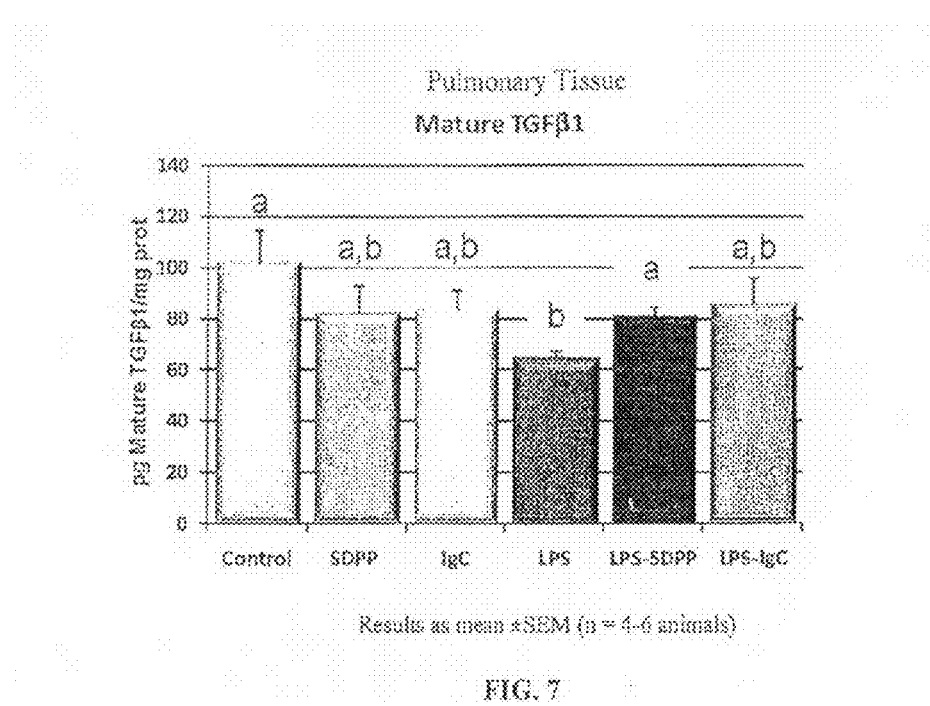
FIG. 7 is a graph depicting modification of mature TGFβ1 in accordance with Example 1.
Figure 8:
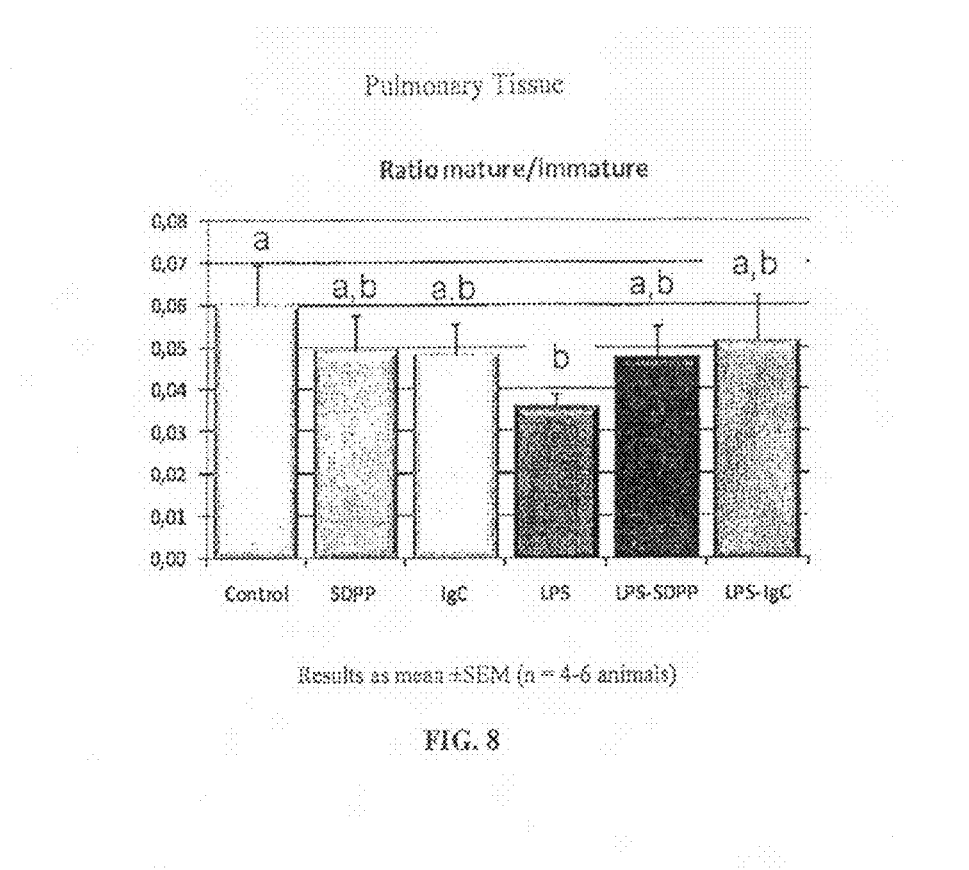
FIG. 8 is a graph depicting the ratio of modification of mature to immature TGFβ1 in accordance with Example 1.
Figure 9:
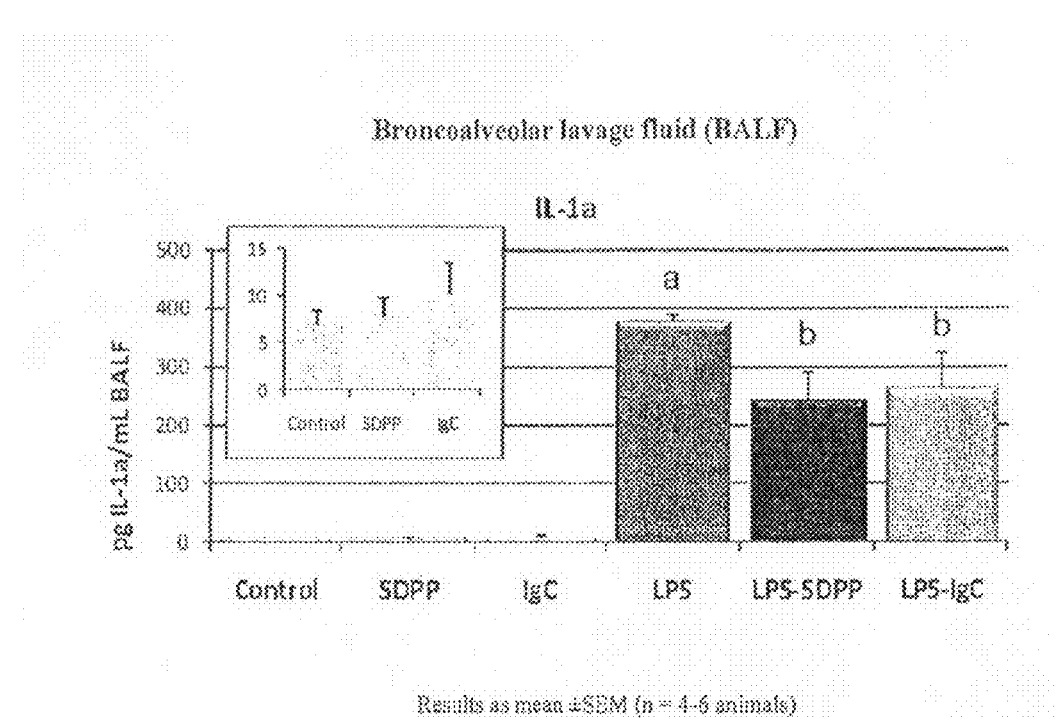
FIG. 9 is a graph depicting modification of Il-1a concentrations in broncoalveolar lavage fluid (BALF) in accordance with Example 1.
Figure 10:
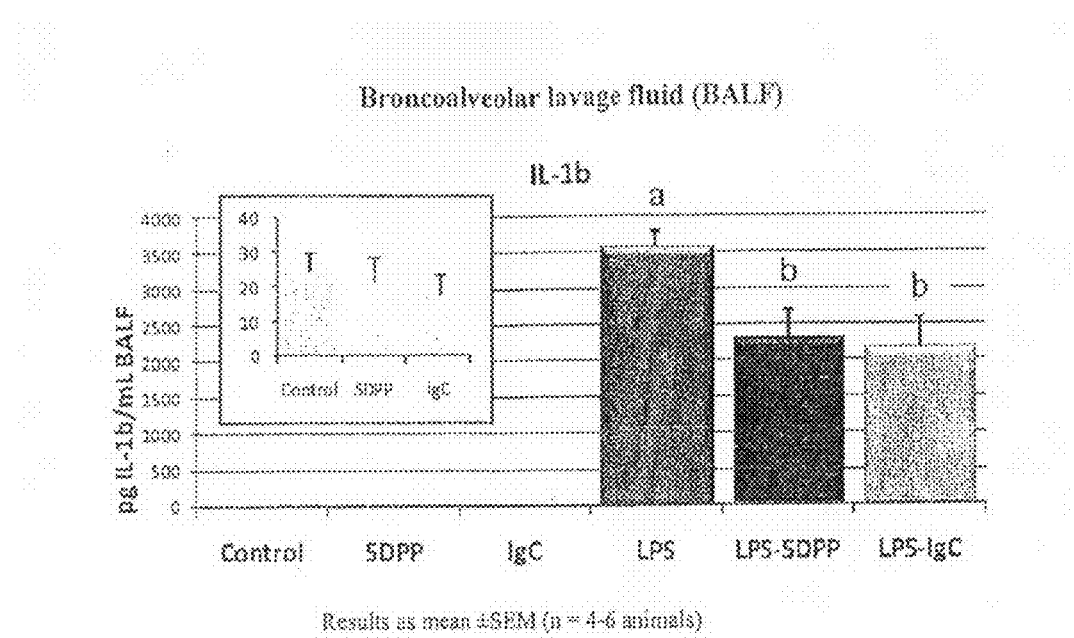
FIG. 10 is a graph depicting modification of Il-1b concentrations in BALF in accordance with Example 1.
Figure 11:
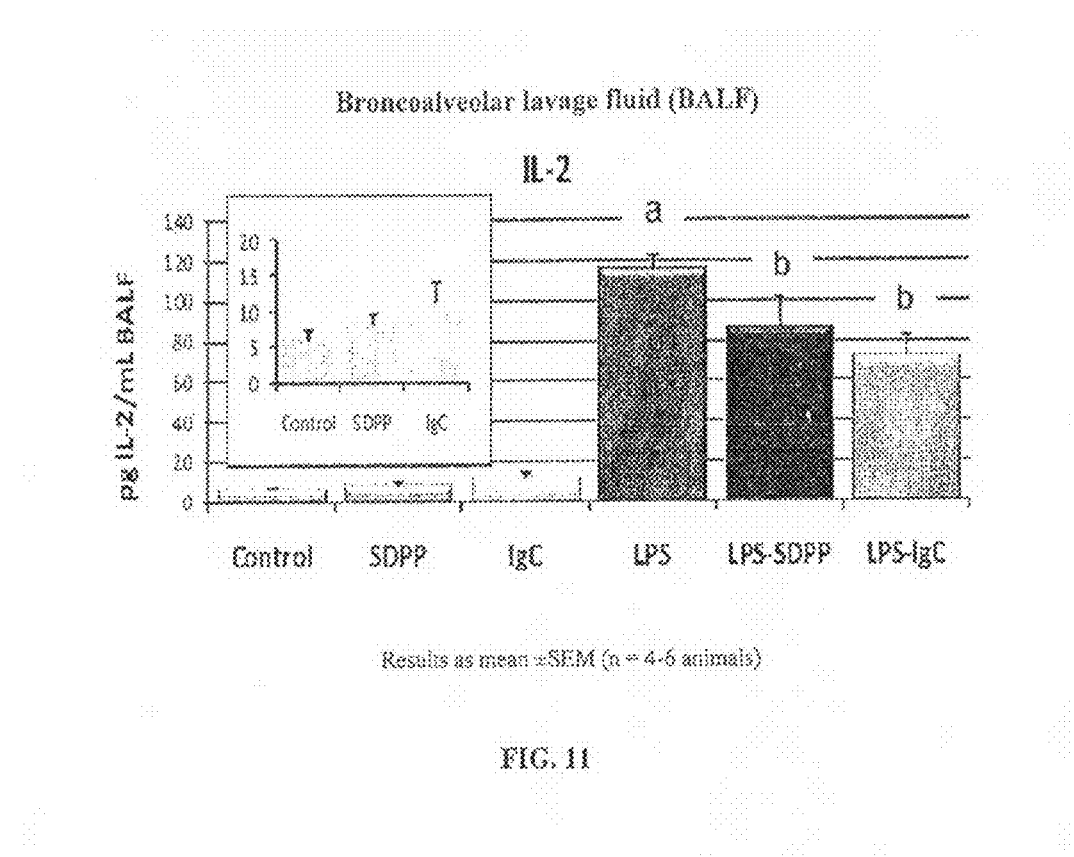
FIG. 11 is a graph depicting modification of Il-2 concentrations in BALF in accordance with Example 1.
Figure 12:
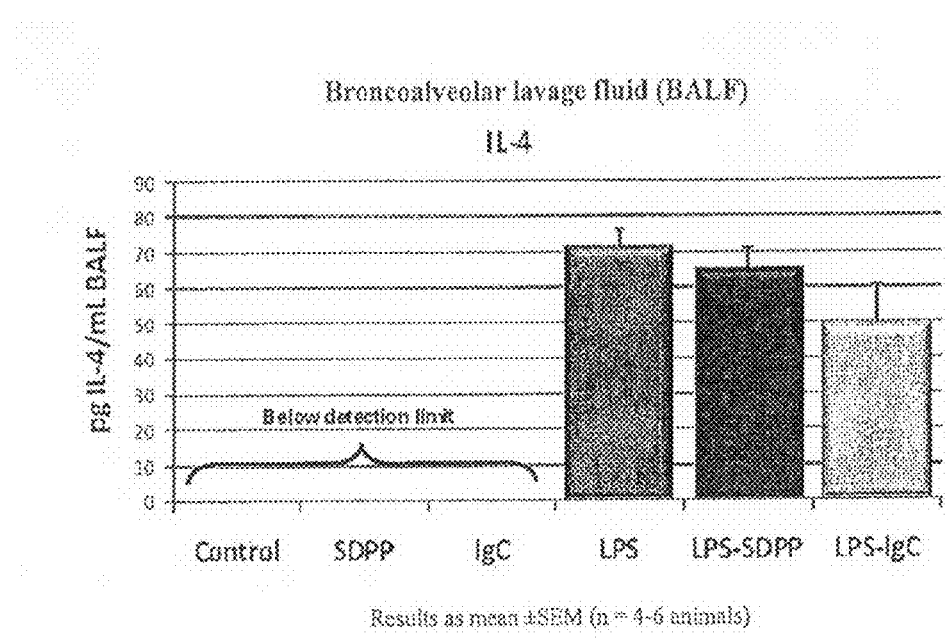
FIG. 12 is a graph depicting modification of Il-4 concentrations in BALF in accordance with Example 1.
Figure 13:
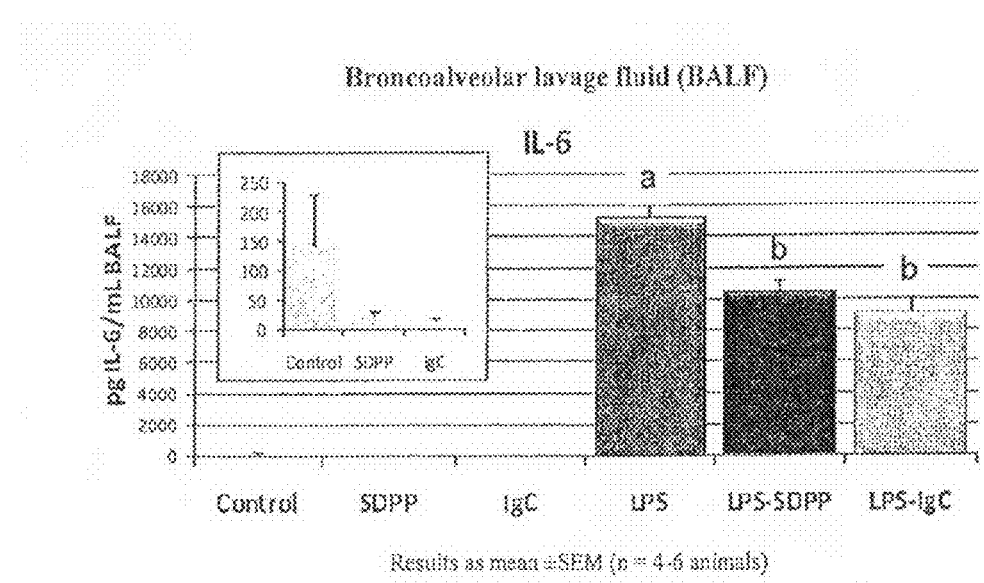
FIG. 13 is a graph depicting modification of Il-6 concentrations in BALF in accordance with Example 1.
Figure 14:
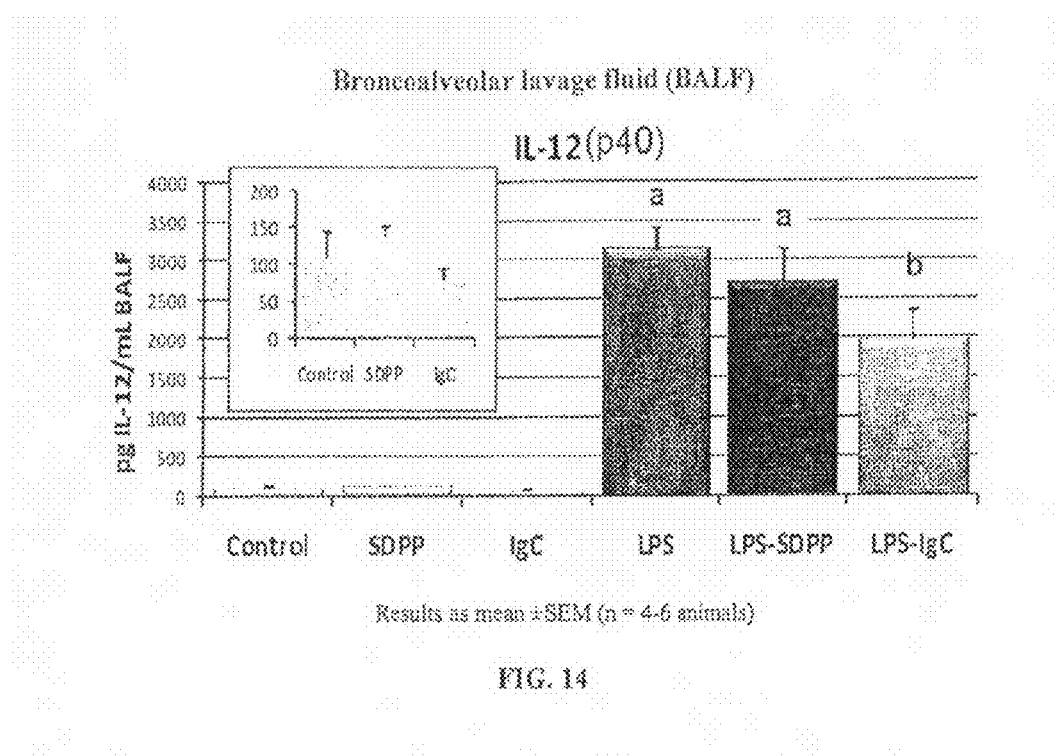
FIG. 14 is a graph depicting modification of Il-12 (p40) concentrations in BALF in accordance with Example 1.
Figure 15:
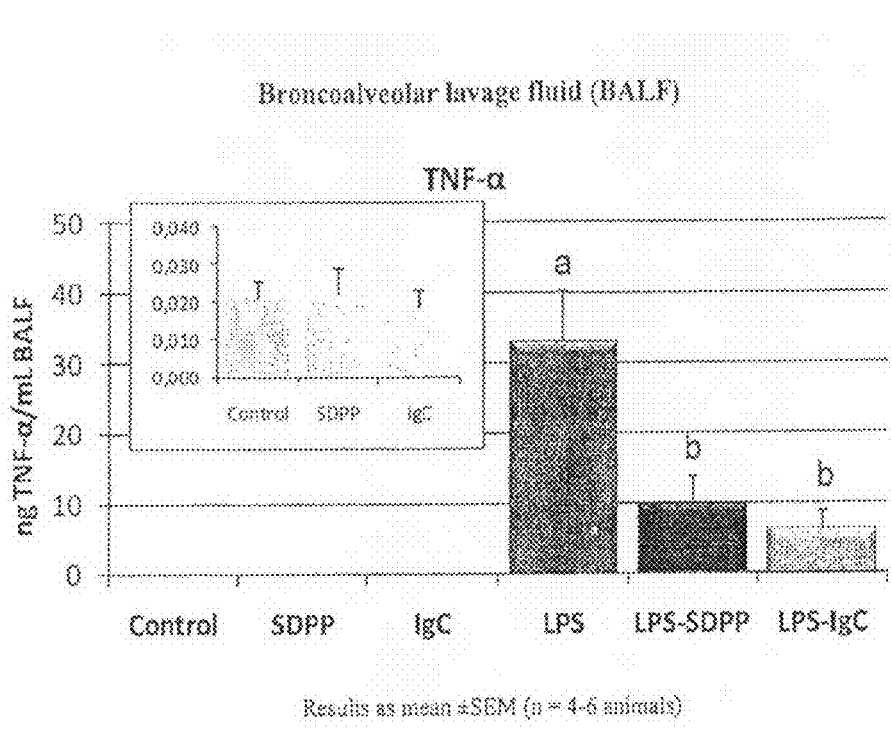
FIG. 15 is a graph depicting modification of TNF-α concentrations in BALF in accordance with Example 1.

LPS administration affects TGFβ1 processing (the mature form is reduced) but does not affect the expression of the precursor protein (total TGFβ1 is not modified). (FIGS. 5-8). SDPP prevents LPS-induced reduction in mature TFGβ1. (FIG. 7).

LPS increases the release of pro-inflammatory cytokines, such as IL-1, TNF-α, IL-6 and IL-12 into the lung airway (BALF) (FIGS. 9-15). Dietary plasma prevents the LPS-induced increase of Th1 pro-inflammatory cytokines without affecting IL-12 production.

LPS also increases IL-2 concentration (it induces CD4 activation through IL-2R), which is prevented by both dietary supplements.

LPS also stimulates the production of Th2 cytokines (IL-4). Neither SDPP nor PF have significant effects on this variable.

These results are further detailed in FIGS. 2-15.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

All publications, patents and patent applications cited herein are herein incorporated by reference.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A method of reducing pulmonary inflammation in an animal comprising: administering to an animal having pulmonary inflammation an effective amount of a plasma fraction comprising at least 30% by weight IgG and 10% or less by weight IgA, wherein the plasma fraction is administered to provide a dose range from about 10 mg to 500 mg per kg body weight per day, and whereby the plasma fraction is administered intrapulmonarily.

2. The method of claim 1 whereby the plasma fraction is administered in a pharmaceutically acceptable aerosol.

3. The method of claim 2 whereby the plasma fraction is administered through a nebulizer.

4. A method of reducing pulmonary inflammation in an animal comprising: administering to an animal having LPS-induced pulmonary inflammation an effective amount of a plasma fraction comprising at least 30% by weight IgG and 10% or less by weight IgA; whereby the plasma fraction is administered in a pharmaceutically acceptable aerosol, and further providing that the plasma fraction is administered to provide a dose range from about 10 mg to 500 mg per kg body weight per day.

5. The method of claim 4 whereby the plasma fraction comprises at least 40% by weight IgG and 2% or less by weight IgA.

6. A method of reducing pulmonary inflammation in an animal comprising: administering to an animal having LPS-induced pulmonary inflammation an effective amount of a plasma fraction comprising at least 40% by weight IgG, said plasma fraction containing undetectable levels of IgA; wherein the plasma fraction is administered to provide a dose range from about 10 mg to 500 mg per kg body weight per day.

* * * * *